US012582458B2

(12) United States Patent
Kaneko

(10) Patent No.: US 12,582,458 B2
(45) Date of Patent: Mar. 24, 2026

(54) PUNCTURING DEVICE

(71) Applicant: KANEKA CORPORATION, Osaka (JP)

(72) Inventor: Takuya Kaneko, Okaya (JP)

(73) Assignee: KANEKA CORPORATION, Osaka (JP)

( * ) Notice: Subject to any disclaimer, the term of this patent is extended or adjusted under 35 U.S.C. 154(b) by 406 days.

(21) Appl. No.: 18/035,965

(22) PCT Filed: Oct. 12, 2021

(86) PCT No.: PCT/JP2021/037699
§ 371 (c)(1),
(2) Date: May 9, 2023

(87) PCT Pub. No.: WO2022/102319
PCT Pub. Date: May 19, 2022

(65) Prior Publication Data

US 2023/0404649 A1 Dec. 21, 2023

(30) Foreign Application Priority Data

Nov. 12, 2020 (JP) ................................ 2020-188783

(51) Int. Cl.
*A61B 18/14* (2006.01)
*A61M 25/00* (2006.01)
*A61B 18/00* (2006.01)

(52) U.S. Cl.
CPC .......... *A61B 18/14* (2013.01); *A61B 18/1492* (2013.01); *A61M 25/00* (2013.01); *A61B 2018/00351* (2013.01)

(58) Field of Classification Search
CPC .................. A61B 18/1492; A61B 2018/00351
See application file for complete search history.

(56) References Cited

U.S. PATENT DOCUMENTS 8,794,629 B1 8/2014 Humphreys, Jr.
2004/0143261 A1 7/2004 Hartley et al.
(Continued)

FOREIGN PATENT DOCUMENTS

JP 2015-518752 A 7/2015
JP 2016-509942 A 4/2016
(Continued)

OTHER PUBLICATIONS

International Search Report (PCT/ISA/210), issued in PCT/JP2021/037699, dated Dec. 7, 2021.
(Continued)

*Primary Examiner* — Sean W Collins
(74) *Attorney, Agent, or Firm* — Birch, Stewart, Kolasch & Birch, LLP

(57) ABSTRACT

A puncturing device (1) comprising: a resin tube (10) having a distal end and a proximal end and extending in a longitudinal direction; a metal tube (20) disposed in a lumen of the resin tube (10); a metal core member (30) joined to a distal end portion of the metal tube (20); and a metal tip (40) joined to a distal end portion of the metal core member (30), wherein the puncturing device (1) has a flow path for a liquid, between an inner surface of the resin tube (10) and an outer surface of the metal core member (30), the flow path is in communication with a lumen of the metal tube (20), and the resin tube (10) has, in a side face thereof, an opening (11) that allows communication between the flow path and outside of the resin tube (10).

16 Claims, 4 Drawing Sheets

(56) References Cited

U.S. PATENT DOCUMENTS

2004/0143262 A1 7/2004 Visram et al.
2005/0065507 A1 3/2005 Hartley et al.
2005/0159738 A1 7/2005 Visram et al.
2006/0142756 A1 6/2006 Davies et al.
2007/0066975 A1 3/2007 Wong et al.
2007/0123964 A1 5/2007 Davies et al.
2007/0185522 A1 8/2007 Davies et al.
2008/0086120 A1 4/2008 Mirza et al.
2008/0208121 A1 8/2008 Youssef et al.
2011/0118735 A1 5/2011 Abou-Marie et al.
2011/0224666 A1 9/2011 Davies et al.
2012/0046657 A1 2/2012 Biadillah et al.
2012/0215213 A1 8/2012 Juzkiw et al.
2012/0232546 A1 9/2012 Mirza et al.
2014/0039315 A1 2/2014 Davies et al.
2014/0039484 A1 2/2014 Leung
2014/0100560 A1 4/2014 Biadillah et al.
2014/0100561 A1 4/2014 Biadillah et al.
2014/0206987 A1 7/2014 Urbanski et al.
2015/0216620 A1* 8/2015 Davies .............. A61M 25/0108 606/41
2015/0374431 A1 12/2015 Davies et al.
2016/0000501 A1 1/2016 Davies et al.
2016/0038216 A1 2/2016 Woo et al.
2016/0066989 A1 3/2016 Davies et al.
2016/0262795 A1 9/2016 Urbanski et al.
2016/0374751 A1 12/2016 Davies et al.
2017/0071667 A1 3/2017 Leung et al.
2017/0189113 A1 7/2017 Urbanski et al.
2019/0216528 A1 7/2019 Woo et al.
2019/0231424 A1* 8/2019 Davies ............... A61B 18/1492
2019/0239924 A1 8/2019 Urbanski et al.
2019/0274754 A1 9/2019 Davies et al.
2019/0374281 A1 12/2019 Davies et al.
2020/0345410 A1 11/2020 Davies et al.
2021/0000538 A1 1/2021 Davies et al.
2021/0106400 A1 4/2021 Davies et al.
2021/0121227 A1 4/2021 Davies et al.
2021/0307823 A1 10/2021 Urbanski et al.
2021/0338318 A1 11/2021 Davies et al.
2021/0369336 A1 12/2021 Davies et al.
2022/0151681 A1 5/2022 Leung et al.
2022/0240979 A1 8/2022 Urbanski et al.
2022/0354572 A1 11/2022 Davies et al.

FOREIGN PATENT DOCUMENTS

JP 2016-513520 A 5/2016
JP 2019-30693 A 2/2019

OTHER PUBLICATIONS

Written Opinion of the International Searching Authority (PCT/ISA/237), issued in PCT/JP2021/037699, dated Dec. 7, 2021.

* cited by examiner

[Fig. 1]
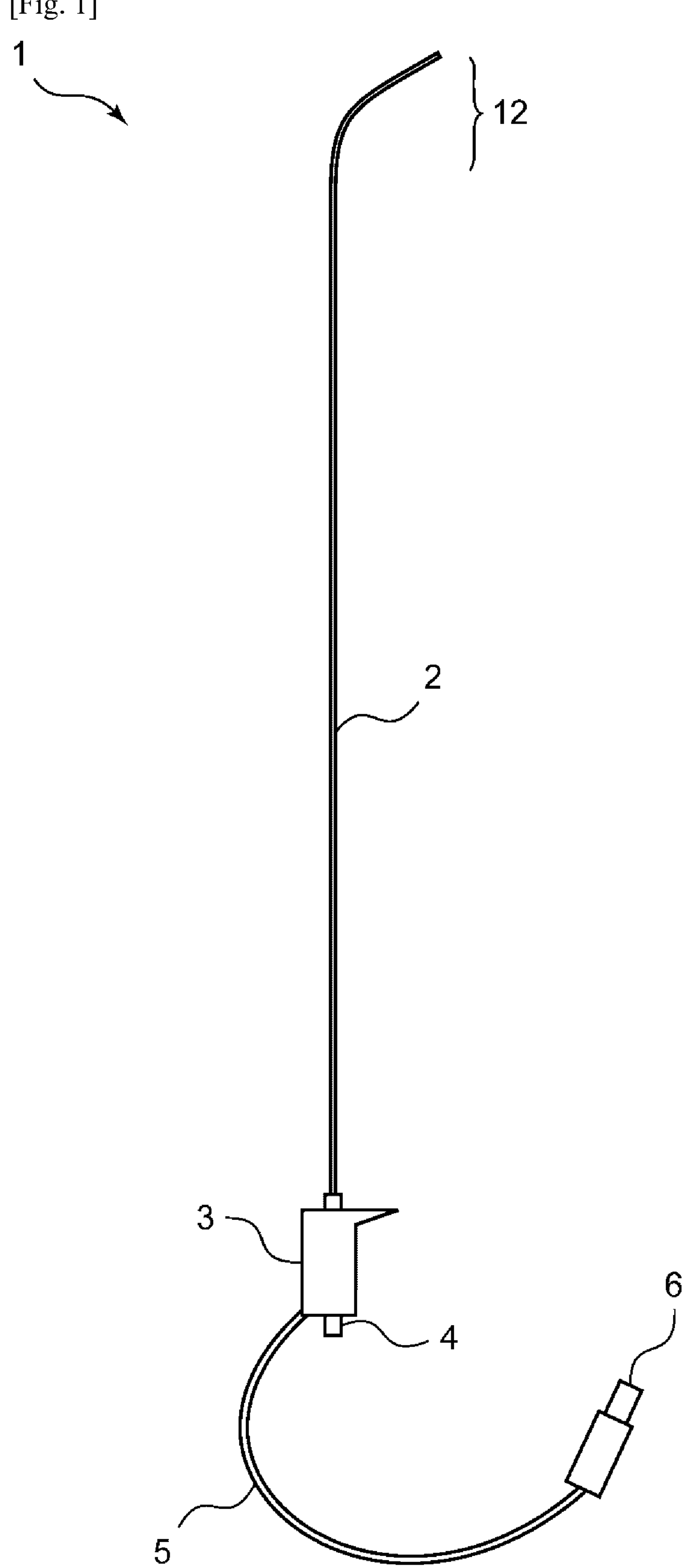

[Fig. 2]
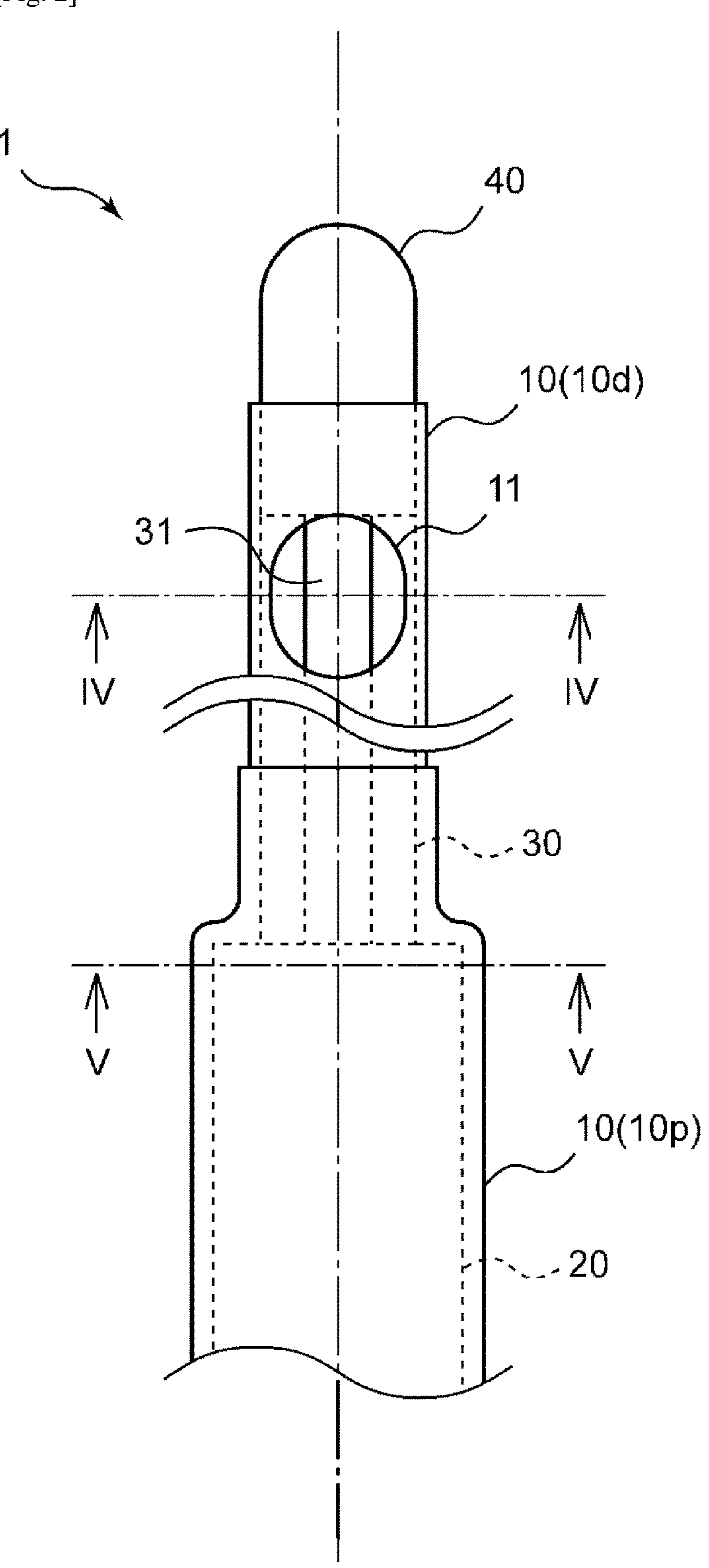

[Fig. 3]
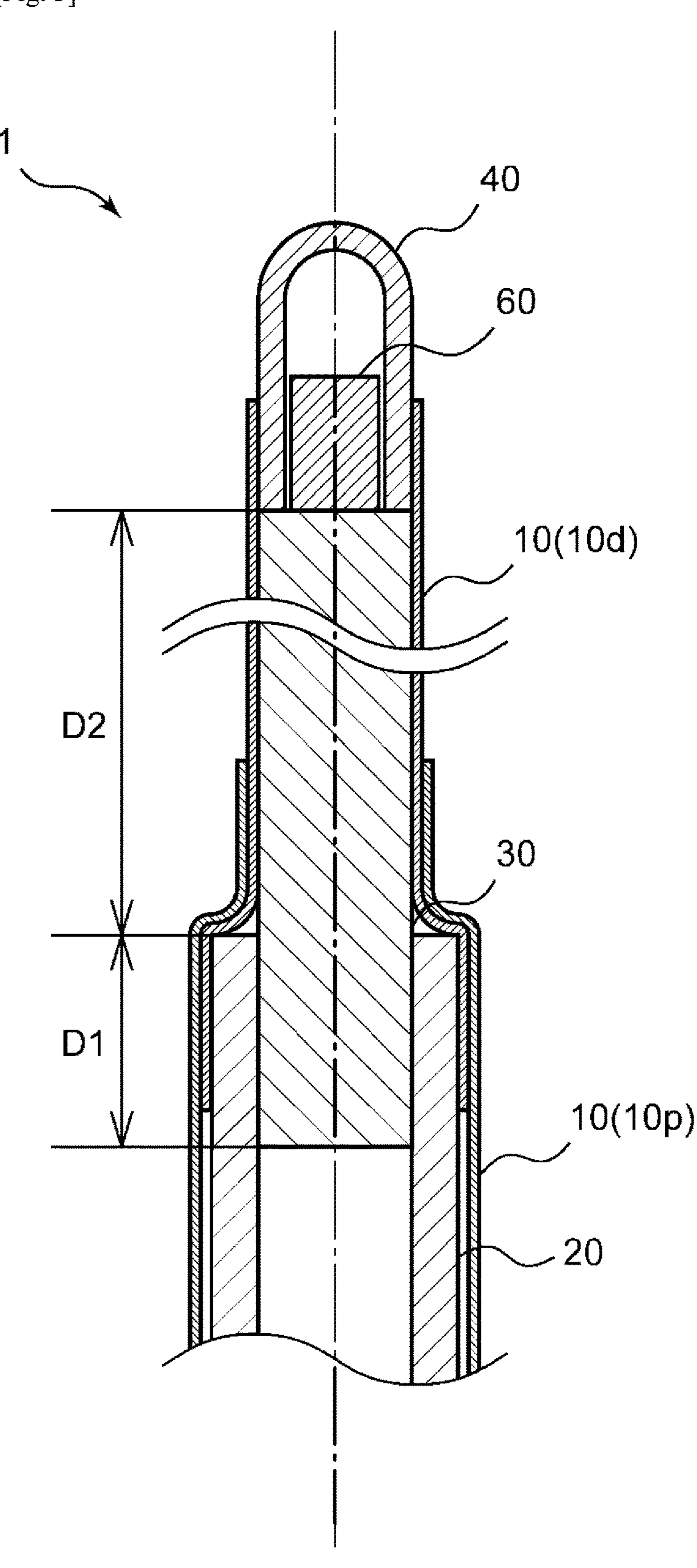

[Fig. 4]
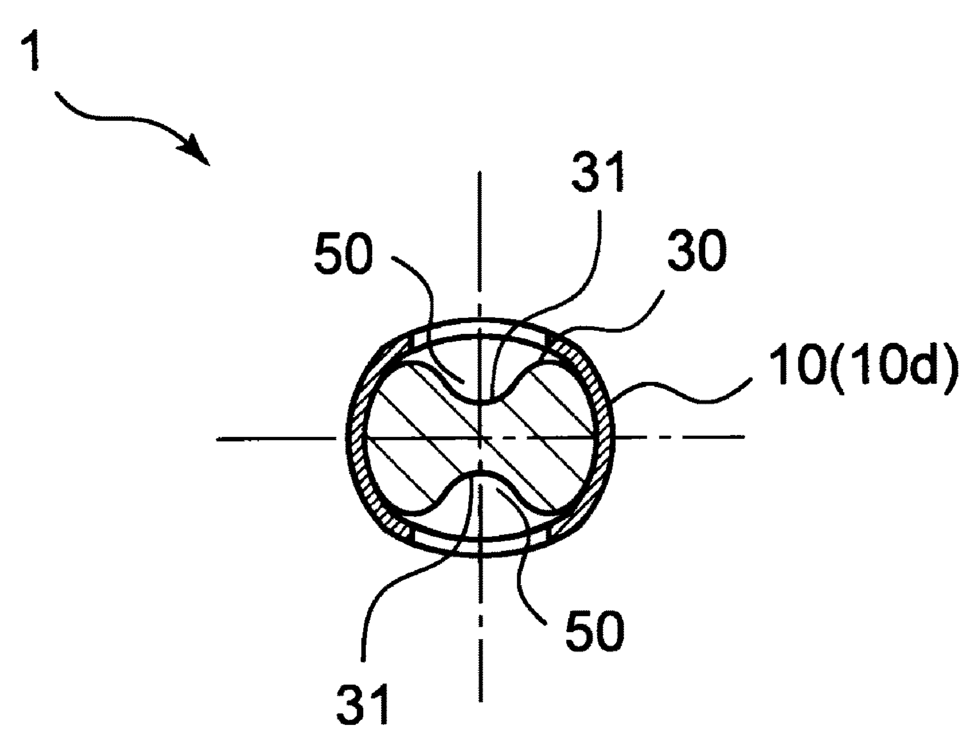
[Fig. 5]
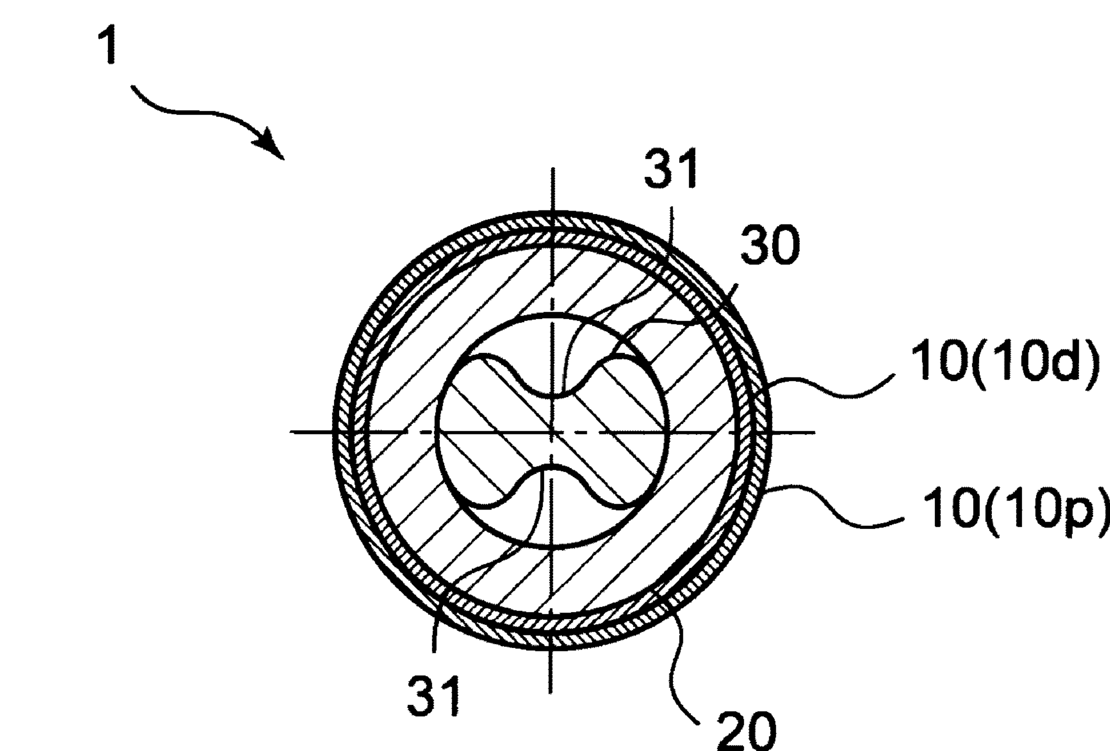

PUNCTURING DEVICE

TECHNICAL FIELD

The present invention relates to a puncturing device that punctures a biotissue such as a septum part of an atrium.

BACKGROUND ART

In a checkup or a therapy for arrhythmia such as atrial fibrillation (AF) or atrioventricular reciprocating tachycardia (AVRT), a catheter having electrodes is used. During the checkup, an operator inserts the electrode catheter into a heart chamber, and measures an intracardiac potential to identify an abnormal site, of the heart, that is the cause of the arrhythmia. During the therapy, the operator performs a so-called ablation surgery in which energy including high-frequency current is caused to flow from the electrodes of the catheter to a cardiac muscle that is the cause of the arrhythmia, thereby necrotizing the source of the arrhythmia to be electrically separated from the heart. Meanwhile, if atrial fibrillation has naturally occurred or atrial fibrillation has been caused to occur in order to identify the abnormal site of the heart during the checkup or the therapy, the operator performs defibrillation by applying electrical stimulation from the electrodes of the catheter to the heart.

When an ablation surgery is performed, the Brockenbrough method is used. The Brockenbrough method is a puncture method in which, in order to deliver the catheter from the right atrium side to the left atrium side, a fossa ovalis in the septum part between the atria is punctured from the right atrium by using a Brockenbrough needle (septum puncture needle), to open an insertion path for the catheter.

In the Brockenbrough method, the leading end of the septum puncture needle is pressed against the fossa ovalis while the positions of the fossa ovalis and the device are confirmed by intracardiac echocardiography or X-ray irradiation, and the septum puncture needle is energized to cauterize and penetrate the fossa ovalis. In a state where the fossa ovalis is penetrated by the septum puncture needle, a liquid such as a saline or a contrast medium is caused to flow from the leading end of the septum puncture needle, the liquid is confirmed to flow to the left atrium side, by using intracardiac echocardiography or X-ray irradiation, and the presence or absence of a puncture hole in the fossa ovalis is checked.

Examples of the septum puncture needle to be used in the Brockenbrough method include the following. A medical device including: a metal elongated member having a proximal end portion and a distal end portion, the elongated member defining a lumen substantially extending between the proximal end portion and the distal end portion, the elongated member defining at least one opening from the lumen; and a contrast marker associated with the elongated member at a marker position and configured so as to substantially prevent hindrance of a flow of a fluid passing through the lumen during use, the outer diameter of the device at the marker position being substantially equal to the outer diameter of the device adjacent to the marker position (see Patent Literature 1, for example). A medical device including: a flexible elongated member configured to cross a lumen in a body and defining a lumen in communication with at least one distal aperture; and a support spine proximally extending from the distal end of the medical device, in a distal portion of the lumen, wherein the proximal end of the support spine is disposed in the distal portion of the lumen (see Patent Literature 2, for example). An energy delivery device including: an elongated member defining a lumen for allowing a fluid to pass therethrough; and a distal face of the elongated member defining an opening in communication with the lumen, the distal face including at least one electrically exposed conductive portion and at least one electrically insulated portion, wherein the distal face is configured to avoid generation of emboli during delivery of energy via the electrically exposed conductive portion (see Patent Literature 3, for example).

CITATION LIST

Patent Literature

PATENT LITERATURE 1: JP 2015-518752 T
PATENT LITERATURE 2: JP 2016-509942 T
PATENT LITERATURE 3: JP 2016-513520 T

SUMMARY OF INVENTION

Technical Problem

In some cases, in order to facilitate confirmation of the presence or absence of a puncture hole in the fossa ovalis, the flow rate of the liquid such as a saline flowing out from the leading end of the puncture needle is required to be increased. In order to increase the flow rate of the liquid flowing out from the puncture needle, the number of openings serving as the outlet of the liquid may be increased, or the size of the opening may be increased, for example. However, in the puncture needles as in Patent Literatures 1 to 3, when the opening is increased in number or size, the strength of the part where the opening is formed is decreased. Therefore, when the leading end of the puncture needle is pressed against the fossa ovalis, a leading end portion may bend, which may result in difficulty in puncturing the fossa ovalis.

In the puncture needles as in Patent Literatures 1 to 3, processing such as forming an opening in a leading end portion is difficult to be performed, the number of production steps is also large, and thus, the degree of difficulty in production is high. Therefore, there is room for improvement in production of the puncture needle.

The present invention has been made in consideration of the circumstances described above. An object of the present invention is to provide a puncturing device that allows easy production and that allows increase in the strength of a leading end portion of the puncturing device even when the opening is increased in size or number in order to increase the flow rate of a liquid that is discharged by the puncturing device.

Solution to Problem

A puncturing device, which solves the above problem, comprises: a resin tube having a distal end and a proximal end and extending in a longitudinal direction; a metal tube disposed in a lumen of the resin tube; a metal core member joined to a distal end portion of the metal tube; and a metal tip joined to a distal end portion of the metal core member, wherein the puncturing device has a flow path for a liquid, between an inner surface of the resin tube and an outer surface of the metal core member, the flow path is in communication with a lumen of the metal tube, and the resin tube has, in a side face thereof, an opening that allows communication between the flow path and outside of the resin tube.

In the puncturing device of the present invention, it is preferable that in a section where the flow path is present, a portion of the outer surface of the metal core member is in contact with the inner surface of the resin tube along the longitudinal direction.

In the puncturing device of the present invention, it is preferable that in a cross section perpendicular to the longitudinal direction, a cross-sectional area of the metal core member is larger than a cross-sectional area of the flow path.

In the puncturing device of the present invention, it is preferable that the metal core member has a recessed portion extending in the longitudinal direction.

In the puncturing device of the present invention, it is preferable that the metal core member has a plurality of the recessed portions.

In the puncturing device of the present invention, it is preferable that the metal core member is in contact, in a planar manner, with an inner surface of the metal tube.

In the puncturing device of the present invention, it is preferable that in a cross section perpendicular to the longitudinal direction, the metal core member is in contact, in a planar manner and at a plurality of places, with the inner surface of the metal tube.

In the puncturing device of the present invention, it is preferable that in a cross section perpendicular to the longitudinal direction, the metal core member is in contact, in a planar manner and at a plurality of places, with the inner surface of the resin tube.

In the puncturing device of the present invention, it is preferable that on a distal side relative to a distal end of the metal tube, the metal core member has an outer surface that is in contact with the inner surface of the resin tube.

In the puncturing device of the present invention, it is preferable that a distal end of the metal core member is on a proximal side relative to the distal end of the resin tube.

In the puncturing device of the present invention, it is preferable that a distance from a distal end of the metal tube to a proximal end of the metal core member is smaller than a distance from the distal end of the metal tube to a distal end of the metal core member.

In the puncturing device of the present invention, it is preferable that a distal end of the metal tip is on a distal side relative to the distal end of the resin tube.

In the puncturing device of the present invention, it is preferable that the metal tip has an inner cavity, and a X-ray opaque marker is disposed in the inner cavity of the metal tip.

In the puncturing device of the present invention, it is preferable that the opening is on a distal side relative to a distal end of the metal tube.

Advantageous Effects of Invention

The puncturing device of the present invention has a flow path for a liquid, between the inner surface of the resin tube and the outer surface of the metal core member, the flow path is in communication with the lumen of the metal tube, and the resin tube has, in the side face thereof, an opening that allows communication between the flow path and the outside of the resin tube. Therefore, even when the opening is increased in size or number in order to increase the flow rate of the liquid that is discharged by the puncturing device, the strength of the distal end portion of the puncturing device can be maintained. Further, since the puncturing device has the resin tube, the metal tube, the metal core member, and the metal tip, production of the puncturing device is facilitated.

BRIEF DESCRIPTION OF DRAWINGS

FIG. 1 shows a plan view of a puncturing device in an embodiment of the present invention.

FIG. 2 shows a plan view of a distal end portion of the puncturing device shown in FIG. 1.

FIG. 3 shows a cross-sectional view along the longitudinal direction of the puncturing device shown in FIG. 2.

FIG. 4 shows a IV-IV cross-sectional view of the puncturing device shown in FIG. 2.

FIG. 5 shows a V-V cross-sectional view of the puncturing device shown in FIG. 2.

DESCRIPTION OF EMBODIMENTS

Hereinafter, the present invention is specifically described below based on the following embodiments; however, the present invention is not restricted by the embodiments described below of course, and can be certainly put into practice after appropriate modifications within in a range meeting the gist of the above and the below, all of which are included in the technical scope of the present invention. In the drawings, hatching or a reference sign for a member may be omitted for convenience, and in such a case, the description and other drawings should be referred to. In addition, sizes of various members in the drawings may differ from the actual sizes thereof, since priority is given to understanding the features of the present invention.

FIG. 1 is a plan view of a puncturing device 1 in an embodiment of the present invention. FIG. 2 is a plan view of a distal end portion of the puncturing device 1. FIG. 3 is a cross-sectional view along the longitudinal direction of the puncturing device 1. FIG. 4 and FIG. 5 are cross-sectional views perpendicular to the longitudinal direction of the puncturing device 1. The longitudinal direction of the puncturing device 1 can be referred to as the distal-proximal direction of the puncturing device 1.

The puncturing device 1 of the present invention includes: a resin tube 10 having a distal end and a proximal end and extending in the longitudinal direction; a metal tube 20 disposed in a lumen of the resin tube 10; a metal core member 30 joined to a distal end portion of the metal tube 20; and a metal tip 40 joined to a distal end portion of the metal core member 30. The puncturing device 1 has a flow path 50 for a liquid, between the inner surface of the resin tube 10 and the outer surface of the metal core member 30. The flow path 50 is in communication with a lumen of the metal tube 20, and the resin tube 10 has, in a side face thereof, an opening 11 that allows communication between the flow path 50 and the outside of the resin tube 10.

The puncturing device 1 is used, for example, in order to puncture the fossa ovalis being a septum part between atria, to open an insertion path for delivering a catheter to be used in an ablation surgery or the like, from the right atrium to the left atrium.

In the present invention, the proximal side means the near side of a user with respect to the extending direction of the puncturing device 1, and the distal side means the opposite side to the proximal side, i.e., the treatment target side. The extending direction of the puncturing device 1 is referred to as the longitudinal direction. In FIG. 1 to FIG. 3, the lower side of the figure is the proximal side, and the upper side of the figure is the distal side.

As shown in FIG. 1 and FIG. 2, the puncturing device 1 has a shaft 2 including the resin tube 10, the metal tube 20, the metal core member 30, and the metal tip 40, and may have a handle 3 at a proximal end portion of the shaft 2. The handle 3 preferably has a syringe port 4 for sending a liquid such as a saline or a contrast medium to the flow path 50 through the shaft 2. When the handle 3 has the syringe port 4, the liquid can be sent to the flow path 50 by connecting a syringe or the like to the syringe port 4. This facilitates an operation of injecting the liquid into the body from the leading end of the puncturing device 1 in order to confirm the presence or absence of a puncture hole in the fossa ovalis.

The handle 3 preferably has, via a cable 5, a connector 6 for energizing the shaft 2. When the handle 3 has the cable 5 and the connector 6, if the connector 6 is connected to a power supply for high-frequency current energization, the metal tube 20, the metal core member 30, and the metal tip 40 of the shaft 2 can be electrically connected. Accordingly, energization from the metal tip 40 to a counter electrode plate is enabled, and puncturing of the fossa ovalis is facilitated.

The shaft 2 preferably has, in a distal end portion thereof, a bent portion 12 where the shaft 2 is bent. When the shaft 2 has the bent portion 12 in the distal end portion, the puncturing device 1 can be easily inserted into the heart. The angle of the bend of the shaft 2 in the bent portion 12 can be adapted to the shape or state of the heart or a lumen in the body. The bent portion 12 may be positioned on the proximal side relative to the proximal end of the metal core member 30. In addition, the bent portion 12 may be provided in the part where the metal core member 30 is disposed. When the bent portion 12 is provided in a distal portion of the shaft 2, operability of the puncturing device 1 can be improved.

The number of lumens of the resin tube 10 before being assembled as the puncturing device 1 may be a plurality, but is preferably one. When the number of lumens of the resin tube 10 is one, while the outer diameter of the resin tube 10 is made small, the area of the lumen of the resin tube 10 in a cross section perpendicular to the longitudinal direction can be made large. Therefore, the metal tube 20 can be easily disposed in the lumen of the resin tube 10, and production of the puncturing device 1 is facilitated.

As shown in FIG. 2 and FIG. 3, the resin tube 10 has a distal end and a proximal end, and extends in the longitudinal direction. The material forming the resin tube 10 is preferably an insulating material. Examples thereof include synthetic resins including: polyolefin-based resins such as polyethylene and polypropylene; polyamide-based resins such as nylon; polyester-based resins such as PET; aromatic polyether ketone-based resins such as PEEK; polyether polyamide-based resins; polyurethane-based resins; polyimide-based resins; fluorine-based resins such as PTFE, PFA, and ETFE; polyvinyl chloride-based resins; and the like. The resin tube 10 may be formed from a synthetic resin of one type, or may include synthetic resins of a plurality of types. When the material forming the resin tube 10 is an insulating material, the metal tube 20 and the metal core member 30 can be insulated by the resin tube 10 during energization of the metal tip 40. In particular, the material forming the resin tube 10 preferably includes a fluorine-based resin, and more preferably includes PTFE. When the material forming the resin tube 10 includes a fluorine-based resin, slipperiness of the outer surface of the resin tube 10 is increased, and the puncturing device 1 that has good insertability can be obtained.

The length in the longitudinal direction of the resin tube 10 can be selected to be a length appropriate for the therapy, and can be set to not smaller than 500 mm and not larger than 1200 mm, for example.

The outer diameter of the resin tube 10 is preferably not smaller than 0.3 mm, more preferably not smaller than 0.5 mm, and further preferably not smaller than 0.6 mm. When the lower limit value of the outer diameter of the resin tube 10 is set to be in the above-described range, the rigidity of the resin tube 10 is increased, and the puncturing device 1 that has good insertability to a blood vessel can be obtained. Further, the outer diameter of the resin tube 10 is preferably not larger than 2 mm, more preferably not larger than 1.8 mm, and further preferably not larger than 1.5 mm. When the upper limit value of the outer diameter of the resin tube 10 is set to be in the above-described range, the outer diameter of the puncturing device 1 can be made small. Accordingly, the minimal invasiveness of the puncturing device 1 can be improved.

The thickness of the resin tube 10 is preferably not smaller than 50 μm, more preferably not smaller than 100 μm, and further preferably not smaller than 150 μm. When the lower limit value of the thickness of the resin tube 10 is set to be in the above-described range, the metal tube 20 can be insulated by the resin tube 10. Therefore, it is possible to prevent an unintended portion in the body from being cauterized during energization of the metal tip 40. Further, the thickness of the resin tube 10 is preferably not larger than 350 μm, more preferably not larger than 300 μm, and further preferably not larger than 250 μm. When the upper limit value of the thickness of the resin tube 10 is set to be in the above-described range, the outer diameter of the resin tube 10 can be prevented from being too large, and the puncturing device 1 that is minimally invasive can be obtained.

As shown in FIG. 2, FIG. 3, and FIG. 5, the metal tube 20 is disposed in the lumen of the resin tube 10. That is, the resin tube 10 is disposed outside the metal tube 20. The number of the lumens of the metal tube 20 may be a plurality, but is preferably one. When the metal tube 20 has one lumen, the cross-sectional area of the lumen in a direction perpendicular to the longitudinal direction can be made large. Therefore, the flow rate of the liquid to be sent to the flow path 50 can be increased.

Examples of the material forming the metal tube 20 include metals such as stainless steel, carbon steel, and a nickel-titanium alloy. The material forming the metal tube 20 is preferably stainless steel. When the material forming the metal tube 20 is stainless steel, the rigidity of the metal tube 20 is increased, and as a result, the pushability of the puncturing device 1 can be improved.

The length in the longitudinal direction of the metal tube 20 can be selected to be a length appropriate for the therapy, and can be set to not smaller than 500 mm and not larger than 1200 mm, for example.

The outer diameter of the metal tube 20 is preferably not smaller than 0.5 mm, more preferably not smaller than 0.7 mm, and further preferably not smaller than 1 mm. When the lower limit value of the outer diameter of the metal tube 20 is set to be in the above-described range, the rigidity of the metal tube 20 is increased, and the pushability of the puncturing device 1 can be improved. Further, the outer diameter of the metal tube 20 is preferably not larger than 2 mm, more preferably not larger than 1.8 mm, and further preferably not larger than 1.5 mm. When the upper limit value of the outer diameter of the metal tube 20 is set to be in the above-described range, the cross-sectional area of the lumen in a cross section perpendicular to the longitudinal direction of the metal tube 20 can be easily and sufficiently ensured, and the amount of the liquid to be sent to the flow path 50 can be made sufficient.

The thickness of the metal tube 20 is preferably not smaller than 100 μm, more preferably not smaller than 150 μm, and further preferably not smaller than 200 μm. When the lower limit value of the thickness of the metal tube 20 is set to be in the above-described range, the rigidity of the metal tube 20 is increased. Accordingly, when the puncturing device 1 is inserted into a curved lumen in the body and a state where the metal tube 20 is curved is established, the lumen of the metal tube 20 can be prevented from being crushed due to bending of the metal tube 20. Further, the thickness of the metal tube 20 is preferably not larger than 350 μm, more preferably not larger than 300 μm, and further preferably not larger than 250 μm. When the upper limit value of the thickness of the metal tube 20 is set to be in the above-described range, the outer diameter of the metal tube 20 can be prevented from becoming excessively large. As a result, reduction in the diameter of the puncturing device 1 can be realized.

As shown in FIG. 3, the metal core member 30 is joined to a distal end portion of the metal tube 20. Examples of a method for joining the metal core member 30 to the distal end portion of the metal tube 20 include: connection by welding, brazing of solder or the like, bonding, crimping, or the like; press-fitting of the metal core member 30 to the metal tube 20; fitting between the metal tube 20 and the metal core member 30; connection between the metal tube 20 and the metal core member 30 through a separate component; and the like. In particular, the method for joining the metal core member 30 to the distal end portion of the metal tube 20 is preferably fixation such as welding, brazing, or bonding, and more preferably welding. When the distal end portion of the metal tube 20 and the metal core member 30 are fixed to each other, the joining strength between the metal tube 20 and the metal core member 30 is increased. Accordingly, even when the puncturing device 1 is curved, the metal core member 30 is less likely to be detached from the metal tube 20.

As shown in FIG. 3 and FIG. 5, the metal core member 30 is preferably solid. When the metal core member 30 is solid, the rigidity of the distal end portion, of the puncturing device 1, where the metal core member 30 is present is increased. Accordingly, the pushability of the puncturing device 1 can be improved, and puncturing of the fossa ovalis can be easily performed. Examples of the shape of a cross section perpendicular to the longitudinal direction of the metal core member 30 are a circle, an ellipse, a polygon, a cross-shape, an H-shape, a U-shape, an angled shape, and the like.

Examples of the material forming the metal core member 30 include metals such as stainless steel, carbon steel, and a nickel-titanium alloy. The material forming the metal core member 30 is preferably stainless steel. When the material forming the metal core member 30 is stainless steel, the rigidity of the metal core member 30 can be increased. Accordingly, the rigidity of the distal end portion of the puncturing device 1 is also increased, and puncturing of the fossa ovalis can be easily performed.

The outer diameter at the proximal end of the metal core member 30 is preferably smaller than the inner diameter at the distal end of the metal tube 20. When the outer diameter at the proximal end of the metal core member 30 is smaller than the inner diameter at the distal end of the metal tube 20, a proximal end portion of the metal core member 30 can be inserted into the distal end portion of the metal tube 20, and the joining strength between the metal tube 20 and the metal core member 30 can be increased.

As shown in FIG. 2 and FIG. 3, the metal tip 40 is joined to the distal end portion of the metal core member 30. Examples of a method for joining the metal tip 40 to the distal end portion of the metal core member 30 include: connection by welding, brazing of solder or the like, bonding, crimping, or the like; press-fitting of the metal core member 30 to the metal tip 40; fitting between the metal core member 30 and the metal tip 40; connection between the metal core member 30 and the metal tip 40 through a separate component; and the like. In particular, the method for joining the metal tip 40 to the distal end portion of the metal core member 30 is preferably fixation such as welding, brazing, or bonding, and more preferably welding. When the distal end portion of the metal core member 30 and the metal tip 40 are fixed to each other, the metal tip 40 can be rigidly joined to the metal core member 30. Therefore, when the metal tip 40 is pressed against the fossa ovalis when, for example, the fossa ovalis is to be punctured, the metal tip 40 is less likely to fall off from the metal core member 30, and the puncturing device 1 that has a high durability can be obtained.

Examples of the material forming the metal tip 40 include metals such as stainless steel, carbon steel, and a nickel-titanium alloy. The material forming the metal tip 40 is preferably the same as the material forming the metal core member 30. When the material forming the metal tip 40 is the same as the material forming the metal core member 30, joining between the metal core member 30 and the metal tip 40 can be easily performed. In addition, an effect that the joining strength between the metal core member 30 and the metal tip 40 can be increased is also provided.

As shown in FIG. 2 and FIG. 3, the distal end portion of the metal tip 40 preferably has a curved surface shape. When the distal end portion of the metal tip 40 has a curved surface shape, the metal tip 40 is less likely to wound a lumen in the body such as a blood vessel when coming into contact with the lumen in the body, and damage or puncturing at an unintended portion is less likely to be caused.

As described above, since the metal tube 20 and the metal core member 30 of the shaft 2 are joined to each other and the metal core member 30 and the metal tip 40 of the shaft 2 are joined to each other, the three members, i.e., the metal tube 20, the metal core member 30, and the metal tip 40, are electrically connected to each other, and thus can be energized.

As shown in FIG. 4, the puncturing device 1 has the flow path 50 for a liquid, between the inner surface of the resin tube 10 and the outer surface of the metal core member 30. The flow path 50 is in communication with the lumen of the metal tube 20. As shown in FIG. 2, the resin tube 10 has, in the side face thereof, the opening 11 that allows communication between the flow path 50 and the outside of the resin tube 10. That is, the liquid such as a saline or a contrast medium sent into the lumen of the metal tube 20 flows into the flow path 50, to be discharged through the opening 11.

Since the puncturing device 1 has, between the inner surface of the resin tube 10 and the outer surface of the metal core member 30, the flow path 50 in communication with the lumen of the metal tube 20, while the puncturing device 1 is configured to discharge the liquid sent into the lumen of the metal tube 20, from the opening 11, the strength of the distal end portion of the puncturing device 1 can be maintained. Thus, even when the opening 11 is increased in size or the opening 11 is increased in number in order to increase the flow rate of the liquid that is discharged by the puncturing device 1, the strength of the distal end portion of the puncturing device 1 can be maintained. Therefore, even when the puncturing device 1 is pressed against the fossa ovalis when puncturing the fossa ovalis, the distal end portion of the puncturing device 1 is prevented from being bent. In production of the puncturing device 1, by forming the opening 11 in the resin tube 10 after the metal core member 30 has been disposed in the lumen of the resin tube 10, it is possible to cause the flow path 50 in communication with the lumen of the metal tube 20, to be in communication with the outside of the resin tube 10. Therefore, it is not necessary to perform a step of a high degree of difficulty, as in a conventional puncturing device, of making a hole in a side face portion of the metal tube 20 in order to discharge the liquid sent into the lumen of the metal tube 20, to the outside. Thus, production of the puncturing device 1 is facilitated.

Since the opening 11 is provided to the resin tube 10 at the part of the flow path 50, the part without any opening of the resin tube 10 is in contact with the metal core member 30. Thus, since there is the part where the resin tube 10 and the metal core member 30 are in contact with each other, the strength of the puncturing device 1 can be maintained. The resin tube 10 may have flexibility due to the resin material. The shape in a cross section perpendicular to the longitudinal direction of the resin tube 10 before being assembled as the puncturing device 1 may be different from the shape in a cross section perpendicular to the longitudinal direction of the resin tube 10 having been assembled as the puncturing device 1 and having the metal core member 30 disposed in the lumen of the resin tube 10.

As shown in FIG. 4, the number of the flow paths 50 is preferably a plurality. When the number of the flow paths 50 of the puncturing device 1 is a plurality, a large amount of the liquid can be discharged from the puncturing device 1. As a result, confirmation of the presence or absence of a puncture hole in the fossa ovalis by using intracardiac echocardiography or X-ray irradiation can be easily performed.

Preferably, the number of the openings 11 is the same as the number of the flow paths 50 or is larger than the number of the flow paths 50. When the number of the openings 11 is not smaller than the number of the flow paths 50, the amount of the liquid in the flow paths 50 that is discharged through the openings 11 can be increased. Accordingly, confirmation of the presence or absence of a puncture hole in the fossa ovalis can be easily performed. A plurality of the openings 11 may be present on the outer circumference at the same position from the distal end of the resin tube 10, or at different positions from the distal end of the resin tube 10.

As shown in FIG. 2, examples of the shape of the opening 11 viewed from a face perpendicular to the depth direction of the opening 11 include a circle, an ellipse, a polygon, and the like. In particular, the shape of the opening 11 viewed from a face perpendicular to the depth direction of the opening 11 is preferably a circle. When the shape of the opening 11 is a circle, pressure is less likely to be concentrated at a specific place of the edge portion of the opening 11 when the liquid is discharged from the flow path 50 through the opening 11. Accordingly, breakage, e.g., a portion of the opening 11 is torn, can be prevented.

The maximum length of the opening 11 in a face perpendicular to the depth direction of the opening 11 is preferably not smaller than 65%, more preferably not smaller than 70%, and further preferably not smaller than 75% of the outer diameter of the resin tube 10. When the lower limit value of the ratio between the maximum length of the opening 11 and the outer diameter of the resin tube 10 is set to be in the above-described range, the amount of the liquid that can be discharged from the opening 11 becomes sufficient, and confirmation of the presence or absence of a puncture hole in the fossa ovalis by using intracardiac echocardiography or X-ray irradiation can be easily performed. Further, although the upper limit value of the ratio between the maximum length of the opening 11 and the outer diameter of the resin tube 10 is not limited in particular, the maximum length of the opening 11 in a face perpendicular to the depth direction of the opening 11 can be, for example, not larger than 93%, not larger than 90%, or not larger than 88% of the outer diameter of the resin tube 10.

The resin tube 10 may be a single tube from the distal end to the proximal end. As shown in FIG. 2 and FIG. 3, the resin tube 10 may have a distal-side resin tube 10*d* and a proximal-side resin tube 10*p*, the metal core member 30 may be disposed in the lumen of the distal-side resin tube 10*d*, and the metal tube 20 may be disposed in the lumen of the proximal-side resin tube 10*p*. When the resin tube 10 has the distal-side resin tube 10*d* and the proximal-side resin tube 10*p*, the distal-side resin tube 10*d* can be caused to have a size and a material appropriate for the metal core member 30, and the proximal-side resin tube 10*p* can be caused to have a size and a material appropriate for the metal tube 20. Accordingly, a step of disposing the metal tube 20 and the metal core member 30 in the lumen of the resin tube 10 can be easily performed.

As shown in FIG. 3, when the resin tube 10 has the distal-side resin tube 10*d* and the proximal-side resin tube 10*p*, the proximal end of the distal-side resin tube 10*d* is preferably on the proximal side relative to the distal end of the proximal-side resin tube 10*p*. When the proximal end of the distal-side resin tube 10*d* is on the proximal side relative to the distal end of the proximal-side resin tube 10*p*, a proximal end portion of the distal-side resin tube 10*d* and a distal end portion of the proximal-side resin tube 10*p* overlap each other. Therefore, it is possible to prevent blood or the like from entering the lumen of the resin tube 10 through a gap between the distal-side resin tube 10*d* and the proximal-side resin tube 10*p* while the puncturing device 1 is inserted into a lumen in the body.

The length of the part where the proximal end portion of the distal-side resin tube 10*d* and the distal end portion of the proximal-side resin tube 10*p* overlap each other can be selected in consideration of influence on the size of the outer diameter of the resin tube 10 and the joining strength. Examples of a method for joining the proximal end portion of the distal-side resin tube 10*d* and the distal end portion of the proximal-side resin tube 10*p* include heating the proximal end portion of the distal-side resin tube 10*d* and the distal end portion of the proximal-side resin tube 10*p*, bonding the same, and drawing the same.

The proximal end of the distal-side resin tube 10*d* is preferably disposed in the lumen of the proximal-side resin tube 10*p*. When the proximal end of the distal-side resin tube 10*d* is disposed in the lumen of the proximal-side resin tube 10*p*, the distal end portion of the proximal-side resin tube 10*p* can be in close contact with the outer surface of the distal-side resin tube 10*d* as shown in FIG. 3. Therefore, when the liquid has been sent into the lumen of the metal tube 20 and the liquid is passing through the flow path 50, the liquid in the flow path 50 can be less likely to leak out to the outside from between the distal-side resin tube 10*d* and the proximal-side resin tube 10*p*.

Preferably, the proximal end of the distal-side resin tube 10*d* is joined, without a gap, to the distal end of the proximal-side resin tube 10*p*. In a case where the proximal end of the distal-side resin tube 10*d* is joined, without a gap, to the proximal-side resin tube 10*p*, when the metal tip 40 is energized via the metal tube 20, current that is conducted to the metal members, such as the metal tube 20, the metal core member 30, and the metal tip 40, can be less likely to leak out to the outside from a gap between the distal-side resin tube 10*d* and the proximal-side resin tube 10*p*.

As shown in FIG. 2, the outer diameter of the resin tube 10 at the part where the distal end of the metal tube 20 is positioned is preferably larger than the outer diameter of the resin tube 10 at the part where the distal end of the metal core member 30 is positioned. When the outer diameter of the resin tube 10 at the part where the distal end of the metal tube 20 is positioned is larger than the outer diameter of the resin tube 10 at the part where the distal end of the metal core member 30 is positioned, it is possible to form, in the distal end portion of the puncturing device 1, a small diameter portion on the distal side, and a large diameter portion on the proximal side of a medium diameter portion. Therefore, for example, in a case where a dilator is used when the puncturing device 1 is inserted into a lumen in the body, if only the small diameter portion is exposed from the dilator, the length of the puncturing device 1 exposed from the dilator can be easily controlled.

As shown in FIG. 4, in a cross section perpendicular to the longitudinal direction, the cross-sectional area of the metal core member 30 is preferably larger than the cross-sectional area of the flow path 50. When the cross-sectional area of the metal core member 30 is larger than the cross-sectional area of the flow path 50, the rigidity of the part where the metal core member 30 is present in the distal end portion of the puncturing device 1 is increased. Accordingly, the insertability of the puncturing device 1 can be increased.

In a cross section perpendicular to the longitudinal direction, the cross-sectional area of the metal core member 30 is preferably not smaller than 1.1 times, more preferably not smaller than 1.3 times, and further preferably not smaller than 1.5 times the cross-sectional area of the flow path 50. When the lower limit value of the ratio between the cross-sectional area of the metal core member 30 and the cross-sectional area of the flow path 50 is set to be in the above-described range, the rigidity of the distal end portion of the puncturing device 1 where the metal core member 30 is disposed can be sufficiently increased. Further, the cross-sectional area of the metal core member 30 is preferably not larger than 5 times, more preferably not larger than 4 times, and further preferably not larger than 3 times the cross-sectional area of the flow path 50. When the upper limit value of the ratio between the cross-sectional area of the metal core member 30 and the cross-sectional area of the flow path 50 is set to be in the above-described range, the outer diameter of the distal end portion of the puncturing device 1 can be prevented from becoming too large, while the cross-sectional area of the flow path 50 is ensured.

In the section where the flow path 50 is present, a portion of the outer surface of the metal core member 30 is preferably in contact with the inner surface of the resin tube 10 along the longitudinal direction. The part where the outer surface of the metal core member 30 and the inner surface of the resin tube 10 are not in contact with each other serves as the flow path 50, and the part where the outer surface of the metal core member 30 and the inner surface of the resin tube 10 are in contact with each other serves as the part where the strength of the distal end portion of the puncturing device 1 is maintained.

As shown in FIG. 2, FIG. 4, and FIG. 5, the metal core member 30 preferably has a recessed portion 31 extending in the longitudinal direction. The metal core member 30 only needs to have a part that serves as the flow path 50 in the relationship with the resin tube 10. In particular, when the metal core member 30 has the recessed portion 31 extending in the longitudinal direction, the flow path 50 is easily formed between the inner surface of the resin tube 10 and the outer surface of the metal core member 30, and in addition, the cross-sectional area of the flow path 50 can be sufficiently ensured. Accordingly, the amount of the liquid that is discharged from the opening 11 can be made sufficient.

In a cross section perpendicular to the longitudinal direction, the maximum distance between the recessed portion 31 and the inner surface of the resin tube 10 is preferably not smaller than 20%, more preferably not smaller than 25%, and further preferably not smaller than 30% of the maximum length of the metal core member 30. When the lower limit value of the ratio between: the maximum distance between the recessed portion 31 and the inner surface of the resin tube 10; and the maximum length of the metal core member 30 is set to be in the above-described range, the cross-sectional area of the flow path 50 in the cross section perpendicular to the longitudinal direction can be ensured, and the amount of the liquid passing through the flow path 50 can be made sufficient. In a cross section perpendicular to the longitudinal direction, the maximum distance between the recessed portion 31 and the inner surface of the resin tube 10 is preferably not larger than 70%, more preferably not larger than 60%, and further preferably not larger than 50% of the maximum length of the metal core member 30. When the upper limit value of the ratio between: the maximum distance between the recessed portion 31 and the inner surface of the resin tube 10; and the maximum length of the metal core member 30 is set to be in the above-described range, the strength of the metal core member 30 can be maintained, and the rigidity of the distal end portion of the puncturing device 1 where the metal core member 30 is present can be ensured.

As shown in FIG. 4 and FIG. 5, the metal core member 30 preferably has a plurality of the recessed portions 31. When the metal core member 30 has a plurality of the recessed portions 31, the cross-sectional area of the flow path 50 in a cross section perpendicular to the longitudinal direction can be made large, and the amount of the liquid that is discharged from the opening 11 can be increased.

Although not shown, preferably, the metal core member 30 has a first recessed portion and a second recessed portion, and the resin tube 10 has: a first opening that allows communication between a first flow path formed by the first recessed portion and the outside of the resin tube 10; and a second opening that allows communication between a second flow path formed by the second recessed portion and the outside of the resin tube 10. When the metal core member 30 has the first recessed portion and the second recessed portion, and the resin tube 10 has the first opening and the second opening, the respective recessed portions 31 serve as different flow paths, and the liquid can be discharged from the plurality of openings 11 into different directions, respectively. Therefore, the discharge amount of the liquid can be increased, and the liquid can be discharged in a plurality of directions. Thus, confirmation of the presence or absence of a puncture hole in the fossa ovalis by using intracardiac echocardiography or X-ray irradiation is facilitated.

As shown in FIG. 3 and FIG. 5, the metal core member 30 is preferably in contact, in a planar manner, with the inner surface of the metal tube 20. When the metal core member 30 is in contact, in a planar manner, with the inner surface of the metal tube 20, the area of the contact between the metal tube 20 and the metal core member 30 can be made large. Accordingly, the joining strength between the metal tube 20 and the metal core member 30 can be increased, and thus, even in a state where the puncturing device 1 is inserted in a curved lumen in the body, the metal core member 30 can be less likely to be detached from the metal tube 20. In a cross section perpendicular to the longitudinal direction, the length of the planar contact between the metal core member 30 and the inner surface of the metal tube 20 can be selected in consideration of the joining strength between the metal tube 20 and the metal core member 30 and the flow rate of the flow path 50.

In a cross section perpendicular to the longitudinal direction, the length of the planar contact between the metal core member 30 and the inner surface of the metal tube 20 is preferably not smaller than 10%, more preferably not smaller than 20%, and further preferably not smaller than 30% of the length of the outer surface of the metal core member 30. When the lower limit value of the ratio between: the length of the planar contact between the metal core member 30 and the inner surface of the metal tube 20; and the length of the outer surface of the metal core member 30 is set to be in the above-described range, the length of the part where the metal tube 20 and the metal core member 30 are in contact with each other in a cross section perpendicular to the longitudinal direction can be sufficiently ensured, and the joining strength between the metal tube 20 and the metal core member 30 can be improved. When the contact area between the metal core member 30 and the metal tube 20 is defined, it is possible to stabilize the resistance value of current that is conducted in the metal members such as the metal tube 20, the metal core member 30, and the metal tip 40. Further, when the contact area between the metal core member 30 and the metal tube 20 is made large, the resistance value of the puncturing device 1 can be decreased. In a cross section perpendicular to the longitudinal direction, the length of the planar contact between the metal core member 30 and the inner surface of the metal tube 20 is preferably not larger than 70%, more preferably not larger than 60%, and further preferably not larger than 50% of the length of the outer surface of the metal core member 30. When the upper limit value of the ratio between: the length of the planar contact between the metal core member 30 and the inner surface of the metal tube 20; and the length of the outer surface of the metal core member 30 is set to be in the above-described range, a void is provided between the inner surface of the metal tube 20 and the outer surface of the metal core member 30. Accordingly, the liquid in the lumen of the metal tube 20 can flow into the flow path 50 through this void.

As shown in FIG. 5, in a cross section perpendicular to the longitudinal direction, the metal core member 30 is preferably in contact, in a planar manner and at a plurality of places, with the inner surface of the metal tube 20. When the metal core member 30 is in contact, in a planar manner and at a plurality of places, with the inner surface of the metal tube 20, a plurality of voids are provided between the inner surface of the metal tube 20 and the outer surface of the metal core member 30, in a cross section perpendicular to the longitudinal direction in the part where the metal core member 30 is disposed in the lumen of the metal tube 20. That is, through the plurality of voids, the lumen of the metal tube 20 and the flow path 50 are in communication with each other, and the amount of the liquid to be sent to the flow path 50 can be increased.

As shown in FIG. 4, in a cross section perpendicular to the longitudinal direction, the metal core member 30 is preferably in contact, in a planar manner and at a plurality of places, with the inner surface of the resin tube 10. When the metal core member 30 is in contact, in a planar manner and at a plurality of places, with the inner surface of the resin tube 10, a plurality of the flow paths 50 are present. Accordingly, the amount of the liquid that is discharged by the puncturing device 1 from the opening 11 can be increased.

In a cross section perpendicular to the longitudinal direction, the length of the planar contact between the metal core member 30 and the inner surface of the resin tube 10 is preferably not smaller than 10%, more preferably not smaller than 20%, and further preferably not smaller than 30% of the length of the outer surface of the metal core member 30. When the lower limit value of the ratio between: the length of the planar contact between the metal core member 30 and the inner surface of the resin tube 10; and the length of the outer surface of the metal core member 30 is set to be in the above-described range, the length in a cross section perpendicular to the longitudinal direction of the part where the resin tube 10 and the metal core member 30 are in contact with each other can be made sufficient. As a result, the liquid sent into the flow path 50 can be prevented from flowing into the space, between the metal core member 30 and the resin tube 10, that is not the part serving as the flow path 50, and the amount of the liquid to be discharged from the opening 11 can be ensured. In a cross section perpendicular to the longitudinal direction, the length of the planar contact between the metal core member 30 and the inner surface of the resin tube 10 is preferably not larger than 70%, more preferably not larger than 60%, and further preferably not larger than 50% of the length of the outer surface of the metal core member 30. When the upper limit value of the ratio between: the length of the planar contact between the metal core member 30 and the inner surface of the resin tube 10; and the length of the outer surface of the metal core member 30 is set to be in the above-described range, the cross-sectional area of the flow path 50 in a cross section perpendicular to the longitudinal direction can be made large, and the amount of the liquid to be discharged from the opening 11 can be increased.

As shown in FIG. 3, on the distal side relative to the distal end of the metal tube 20, the metal core member 30 preferably has an outer surface that is in contact with the inner surface of the resin tube 10. When the metal core member 30 has, on the distal side relative to the distal end of the metal tube 20, an outer surface that is in contact with the inner surface of the resin tube 10, a part where the inner surface of the resin tube 10 and the outer surface of the metal core member 30 are in close contact with each other can be formed on the distal side relative to the distal end of the metal tube 20. Therefore, while the rigidity of the distal end portion of the puncturing device 1 is ensured, the liquid in the flow path 50 is less likely to flow into a part other than the flow path 50, and the liquid can be efficiently discharged from the opening 11.

As shown in FIG. 3, preferably, the proximal end of the metal core member 30 is on the proximal side relative to the distal end of the metal tube 20, and the distal end of the metal core member 30 is on the proximal side relative to the distal end of the resin tube 10. When the proximal end of the metal core member 30 is on the proximal side relative to the distal end of the metal tube 20, the area of the contact between the inner surface of the metal tube 20 and the outer surface of the metal core member 30 can be made large, and the joining strength between the metal tube 20 and the metal core member 30 can be increased. When the distal end of the metal core member 30 is on the proximal side relative to the distal end of the resin tube 10, the entirety of the metal core member 30 can be covered by the resin tube 10 in the longitudinal direction. Thus, it is possible to guide the liquid sent into the flow path 50 to the opening 11 to be efficiently discharged from the opening 11.

As shown in FIG. 3, a distance D1 from the distal end of the metal tube 20 to the proximal end of the metal core member 30 is preferably smaller than a distance D2 from the distal end of the metal tube 20 to the distal end of the metal core member 30. When the distance D1 is smaller than the distance D2, the rigidity, of the puncturing device 1, of the part from the distal end of the metal tube 20 to the distal end of the metal core member 30 is increased, and at the same time, the rigidity, of the puncturing device 1, of the part where the metal core member 30 is disposed in the lumen of the metal tube 20, i.e., the part from the distal end of the metal tube 20 to the proximal end of the metal core member 30, can be prevented from becoming excessively increased. Therefore, when the puncturing device 1 is to be inserted into a curved lumen in the body, the distal end portion of the puncturing device 1 can be curved along the lumen in the body, and the minimal invasiveness of the puncturing device 1 can be improved.

The distance D1 from the distal end of the metal tube 20 to the proximal end of the metal core member 30 and the distance D2 from the distal end of the metal tube 20 to the distal end of the metal core member 30 can be set as appropriate in consideration of the balance between the strength and the flow rate of the flow path 50. When the distance D2 is long, the joining strength on the distal side of the puncturing device 1 can be more increased. Meanwhile, when the distance D2 is long, the part where the flow rate of the flow path 50 is restricted is long on the distal side of the puncturing device 1, and thus, the liquid may be less likely to flow. In addition, when the distance D2 is long, the contact area between the metal tube 20 and the metal core member 30 is increased, and thus, occurrence of variation in the electrical resistance value should also be taken into consideration.

As shown in FIG. 3, the distal end of the metal tip 40 is preferably on the distal side relative to the distal end of the resin tube 10. When the distal end of the metal tip 40 is on the distal side relative to the distal end of the resin tube 10, the distal end portion of the metal tip 40 is exposed from the resin tube 10. This exposed part of the metal tip 40 functions as an electrode that cauterizes a tissue. In addition, when a proximal end portion of the metal tip 40 is covered by the resin tube 10, an edge-shaped part of the joint part between the metal tip 40 and the metal core member 30 is less likely to be exposed, and it is possible to prevent this edge-shaped part from hitting a heart tissue and damaging the tissue.

As shown in FIG. 3, preferably, the metal tip 40 has an inner cavity, and an X-ray opaque marker 60 is disposed in the inner cavity of the metal tip 40. When the X-ray opaque marker 60 is disposed in the inner cavity of the metal tip 40, the contrast property of the metal tip 40 against X-rays can be increased. Therefore, by using X-rays at the time of using the puncturing device 1, it is possible to easily confirm the position of the metal tip 40 in the body.

As the material forming the X-ray opaque marker 60, a radiopaque substance such as lead, barium, iodine, tungsten, gold, platinum, iridium, a platinum-iridium alloy, stainless steel, titanium, palladium, a cobalt-chromium alloy, or the like can be used, for example. In particular, the radiopaque substance is preferably a platinum-iridium alloy. When the material forming the X-ray opaque marker 60 is a platinum-iridium alloy, the contrast property against X-rays can be increased, and the position of the metal tip 40 can be easily confirmed.

Examples of the shape of the X-ray opaque marker 60 include a cylindrical shape, a polygonal cylindrical shape, a shape having a C-shape in a cross section obtained by making a cutout in a cylinder, a coil shape obtained by winding a wire, a columnar shape, and a polygonal columnar shape. The X-ray opaque marker 60 may be disposed at a location other than the inner cavity of the metal tip 40. The number of the X-ray opaque markers 60 may be one or may be a plurality.

As shown in FIG. 2, the opening 11 is preferably on the distal side relative to the distal end of the metal tube 20. When the opening 11 is on the distal side relative to the distal end of the metal tube 20, the opening 11 is positioned in the part where the metal core member 30 is present. Therefore, while the rigidity of the distal end portion of, the puncturing device 1, where the opening 11 is positioned is maintained, the liquid can be discharged from the distal end portion of the puncturing device 1 through the opening 11.

The opening 11 is preferably on the proximal side relative to the proximal end of the metal tip 40. When the opening 11 is on the proximal side relative to the proximal end of the metal tip 40, the area of the flow path 50 exposed from the opening 11 can be increased without the metal tip 40 being exposed from the opening 11. As a result, the amount of the liquid to be discharged from the opening 11 can be increased. In addition, a shape that serves as an obstacle in the sequence of the flow path 50, i.e., from the flow path 50 to the opening 11, can be eliminated. Thus, an effect that discharge of the liquid from the opening 11 can be stabilized is also provided.

As described above, the puncturing device of the present invention includes: a resin tube having a distal end and a proximal end and extending in a longitudinal direction; a metal tube disposed in a lumen of the resin tube; a metal core member joined to a distal end portion of the metal tube; and a metal tip joined to a distal end portion of the metal core member. The puncturing device has a flow path for a liquid, between an inner surface of the resin tube and an outer surface of the metal core member. The flow path is in communication with a lumen of the metal tube. The resin tube has, in a side face thereof, an opening that allows communication between the flow path and outside of the resin tube. Since the puncturing device of the present invention has this configuration, the strength of the distal end portion of the puncturing device can be increased irrespective of the number or size of the opening, and production of the puncturing device is facilitated.

This application claims priority to Japanese Patent Application No. 2020-188783, filed on Nov. 12, 2020. All of the contents of the Japanese Patent Application No. 2020-188783, filed on Nov. 12, 2020, are incorporated by reference herein.

REFERENCE SIGNS LIST

1: puncturing device
2: shaft
3: handle
4: syringe port

5: cable
6: connector
10: resin tube
**10*d***: distal-side resin tube
**10*p***: proximal-side resin tube
11: opening
12: bent portion
20: metal tube
30: metal core member
31: recessed portion
40: metal tip
50: flow path
60: X-ray opaque marker
D1: distance from the distal end of the metal tube to the proximal end of the metal core member
D2: distance from the distal end of the metal tube to the distal end of the metal core member

The invention claimed is:

1. A puncturing device comprising:
a resin tube having a distal end and a proximal end and extending in a longitudinal direction;
a metal tube disposed in a lumen of the resin tube;
a metal core member joined to a distal end portion of the metal tube; and
a metal tip joined to a distal end portion of the metal core member, wherein
the puncturing device has a flow path for a liquid, between an inner surface of the resin tube and an outer surface of the metal core member,
the flow path is in communication with a lumen of the metal tube,
the resin tube has, in a side face thereof, an opening that allows communication between the flow path and outside of the resin tube, and
the metal core member has a recessed portion extending throughout the entire longitudinal length of the metal core member so that the flow path is formed along the recessed portion of the metal core member.

2. The puncturing device according to claim 1, wherein
in a section where the flow path is present, a portion of the outer surface of the metal core member is in contact with the inner surface of the resin tube along the longitudinal direction.

3. The puncturing device according to claim 1, wherein
in a cross section perpendicular to the longitudinal direction, a cross-sectional area of the metal core member is larger than a cross-sectional area of the flow path.

4. The puncturing device according to claim 1, wherein
the metal core member has a plurality of the recessed portions each extending throughout the entire longitudinal length of the metal core member so that a plurality of the flow paths are formed along the recessed portions of the metal core member.

5. The puncturing device according to claim 1, wherein
the metal tube and the metal core member are configured so that the outer surface of the metal core member is in contact with an inner surface of the metal tube, and the outer surface of the metal core member contacts with and extends along the inner surface of the metal tube at a portion at which the outer surface of the metal core member is in contact with the inner surface of the metal tube.

6. The puncturing device according to claim 5, wherein
in a cross section perpendicular to the longitudinal direction, the outer surface of the metal core member is in contact with the inner surface of the metal tube at a plurality of portions, so that at each of the plurality of portions, the outer surface of the metal core member contacts with and extends along the inner surface of the metal tube.

7. The puncturing device according to claim 1, wherein
in a cross section perpendicular to the longitudinal direction, the outer surface of the metal core member is in contact with the inner surface of the resin tube at a plurality of portions, so that at each of the plurality of portions, the outer surface of the metal core member contacts with and extends along the inner surface of the resin tube.

8. The puncturing device according to claim 1, wherein
on a distal side relative to a distal end of the metal tube, the metal core member has an outer surface that is in contact with the inner surface of the resin tube.

9. The puncturing device according to claim 1, wherein
a proximal end of the metal core member is on a proximal side relative to a distal end of the metal tube, and
a distal end of the metal core member is on a proximal side relative to the distal end of the resin tube.

10. The puncturing device according to claim 1, wherein
a distance from a distal end of the metal tube to a proximal end of the metal core member is smaller than a distance from the distal end of the metal tube to a distal end of the metal core member.

11. The puncturing device according to claim 1, wherein
a distal end of the metal tip is on a distal side relative to the distal end of the resin tube.

12. The puncturing device according to claim 1, wherein
the metal tip has an inner cavity, and
an X-ray opaque marker is disposed in the inner cavity of the metal tip.

13. The puncturing device according to claim 1, wherein
the opening is on a distal side relative to a distal end of the metal tube.

14. The puncturing device according to claim 1, wherein
a proximal end portion of the metal core member is fixed to the distal end portion of the metal tube.

15. The puncturing device according to claim 1, wherein
in a cross section perpendicular to the longitudinal direction, the outer surface of the metal core member is in contact with the inner surface of the metal tube at a plurality of portions, so that at each of the plurality of portions, the outer surface of the metal core member contacts with and extends along the inner surface of the metal tube, and
in a cross section perpendicular to the longitudinal direction, the outer surface of the metal core member is in contact with the inner surface of the resin tube at a plurality of portions, so that at each of the plurality of portions, the outer surface of the metal core member contacts with and extends along the inner surface of the resin tube.

16. The puncturing device according to claim 1, wherein
a proximal end portion of the metal core member is fixed to the distal end portion of the metal tube, and the distal end portion of the metal core member is fixed to a proximal end portion of the metal tip,
in a cross section perpendicular to the longitudinal direction, the outer surface of the metal core member is in contact with the inner surface of the metal tube at a plurality of portions, so that at each of the plurality of portions, the outer surface of the metal core member contacts with and extends along the inner surface of the metal tube,
in a cross section perpendicular to the longitudinal direction, the outer surface of the metal core member is in contact with the inner surface of the resin tube at a plurality of portions, so that at each of the plurality of portions, the outer surface of the metal core member contacts with and extends along the inner surface of the resin tube, and the opening is on a distal side relative to a distal end of the metal tube and on a proximal side relative to the metal tip, so that the recessed portion of the metal core member faces the opening.

* * * * *